United States Patent [19]

Testerman et al.

[11] Patent Number: 5,843,147
[45] Date of Patent: Dec. 1, 1998

[54] IMPLANTABLE EYELID ELECTRODE AND METHOD OF IMPLANTING SAME

[75] Inventors: Roy L. Testerman, New Hope; Donald J. Erickson, Plymouth; Ronald L. Mezera, Burnsville; Johann J. Neisz, Coon Rapids, all of Minn.

[73] Assignee: Medtronic, Inc., Minneapolis, Minn.

[21] Appl. No.: 643,118

[22] Filed: Apr. 30, 1996

[51] Int. Cl.$^6$ ............................................. A61N 1/05
[52] U.S. Cl. ........................................ 607/116; 600/377
[58] Field of Search ......................... 607/116–118, 141, 607/149, 152, 48; 128/639, 642; 600/377, 383

[56] References Cited

U.S. PATENT DOCUMENTS

| 4,603,697 | 8/1986 | Kamerling | 128/421 |
| 4,735,208 | 4/1988 | Wyler et al. | 128/642 |
| 4,768,523 | 9/1988 | Cahalan et al. | 128/785 |
| 4,799,487 | 1/1989 | Bleicher | 123/419 |
| 4,940,065 | 7/1990 | Tanagho et al. | 607/118 |
| 5,109,846 | 5/1992 | Thomas . | |
| 5,154,174 | 10/1992 | Hawlina | 128/642 |
| 5,344,438 | 9/1994 | Testerman et al. | 607/118 |
| 5,522,889 | 6/1996 | Baker | 623/5 |

FOREIGN PATENT DOCUMENTS

| 0 033 643 | 8/1981 | European Pat. Off. | A61N 1/36 |
| 0 586 858 A1 | 3/1994 | European Pat. Off. | A61N 1/05 |
| 2 278 314 | 2/1976 | France | A61F 1/24 |
| 2279376 | 2/1976 | France . | |
| WO 93/20887 | 10/1993 | WIPO | A61N 1/04 |

OTHER PUBLICATIONS

Cummings et al, "An improved electrode for Electroretinography: Design and Standardization" American Journal of Optometry & Physiological Optics, vol. 55, No. 10, pp. 719–724, Oct. 1978.

R.A. Dailey et al., "Eyelid Anatomy", Dermatol. Surg. Oncol., 18, 1023–1027 (1992).

D.A. Ksienski, "A Minimum Profile Uniform Current Density Electrode", IEEE Transactions on Biomedical Engineering, 39, 682–692 (Jul. 1992).

J. Rothstein et al., "Electronic reanimation of facial paralysis—A feasibility study", Otolaryngology, 94, 82–85 (Jan. 1986).

G.M. Salerno et al., "Electrophysiological Study of the Denervated Orbicularis Oculi Muscle in Dogs", Ann. Plast. Surg., 24, 24–31 (Jan. 1990).

R.L. Testerman et al., "Design and Evaluation of Nerve Stimulating Electrodes", Medical Research Engineering, 10, 6–11 (Jan.–Feb. 1971).

D.L. Zealear et al., "Control of Paralysed Axial Muscles by Electrical Stimulation", Acta Otolaryngol., 83 514–527 (1977).

Primary Examiner—Lee S. Cohen
Attorney, Agent, or Firm—Harold R. Patton; Peter Forrest

[57] ABSTRACT

The implantable eyelid electrode apparatus includes a body of nonconductive material having first and second edges and first and second ends. A longitudinal axis extends between the first and second ends and a distance from the longitudinal axis to at least one of the first and second edges decreases towards at least one of the first and second ends. Conductive material is positioned at a surface of the body and at least one lead wire is in electrical contact with the conductive material. Further, the conductive material may include a number of conductive electrodes which are capable of being connected as an anode, a cathode, or left in an open configuration. The conductive electrodes may be strip electrodes positioned perpendicular to the longitudinal axis, and further, the plurality of conductive electrodes may be configured in a guarded multipolar configuration. An electrode device may be implanted in the upper eyelid or the lower eyelid or both. Moreover, a method for implanting an electrode apparatus includes positioning the electrode apparatus adjacent the orbicularis oculi muscle fiber such that the conductive material of the implantable eyelid electrode is adjacent the surface of the muscle fibers. The conductive electrodes, which may be of a strip configuration, are positioned with their length perpendicular to the muscle fibers, when implanted, to promote current passing parallel to the muscle fibers.

50 Claims, 3 Drawing Sheets

IMPLANTABLE EYELID ELECTRODE AND METHOD OF IMPLANTING SAME

FIELD OF THE INVENTION

The present invention relates generally to implantable medical electronic devices. More particularly, the present invention relates to implantable eyelid devices and methods of implanting such eyelid devices.

BACKGROUND OF THE INVENTION

Hemifacial paralysis is a debilitating disorder affecting many patients. The causes of hemifacial paralysis include idiopathic or viral Bell's palsy, parotid gland carcinoma surgery, acoustic tumor surgery, and many others, for example, trauma. While hemifacial paralysis results in generalized disfigurement, one of the most common medical problems is the loss of the blink reflex. The loss of the blink reflex eliminates the intrinsic protection and lubrication of the cornea. Loss of this ocular function inherently puts the cornea at risk for conjunctival drying and development of corneal abrasions. Traditional treatments for this condition include implanted eyelid weights or springs, lubricating eye drops, and surgical suturing or taping of the eyelids shut. Various disadvantages exist for each of these existing treatments. With, for example, the use of implanted eyelid weights, the shifting of the eyelid weight may open the eyelid when the head is at a certain position and it is undesired that the eyelid be open.

Figure 7:
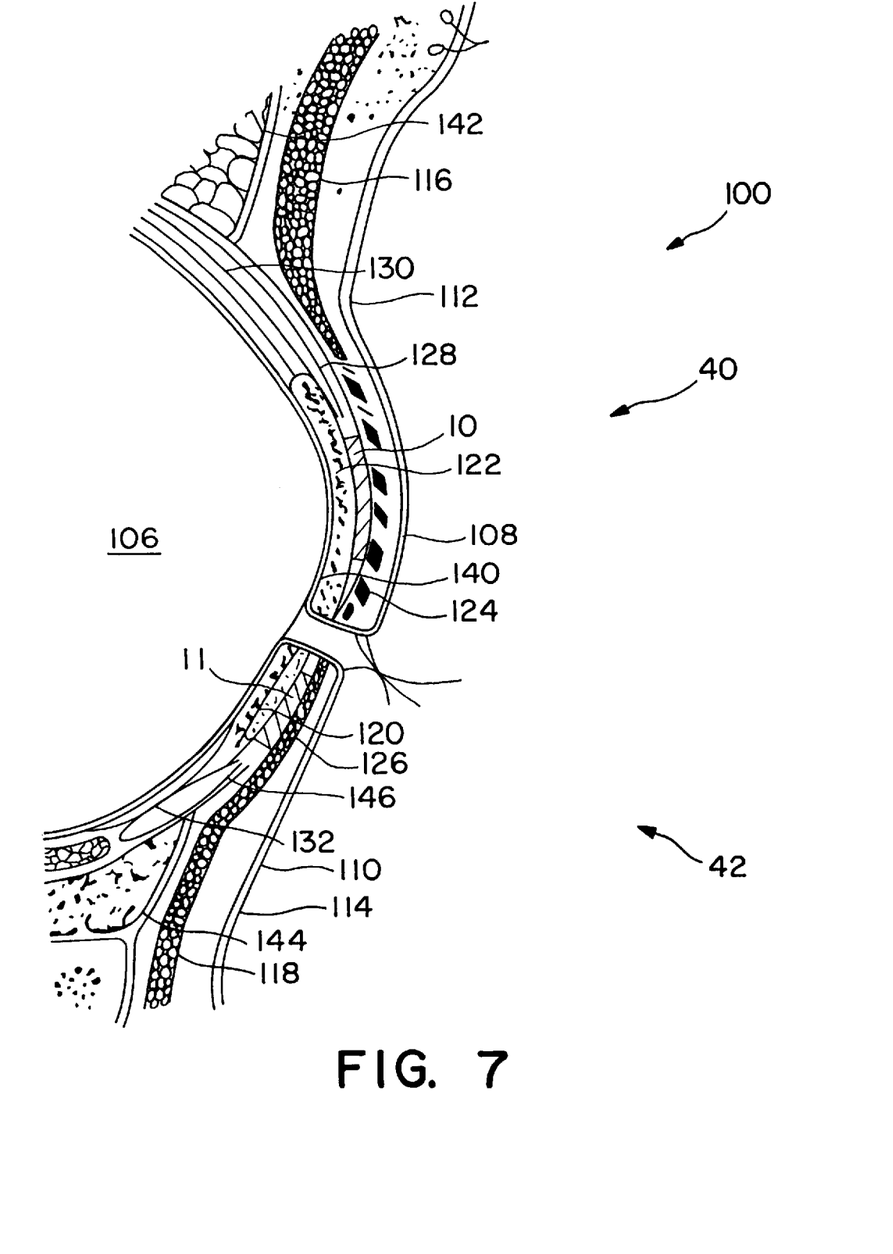
FIG. 7 is a cross sectional view of an eye showing the location of the implantable eyelid electrodes in both the upper eyelid and lower eyelid.

The eyelid of the eye 100 as shown in FIG. 7 includes overlying skin tissue on both the upper and lower eyelid 108, 110. The most posterior layers of the upper 40 and lower eyelids 42 are the tarsus 120, 122 and conjunctiva 140. The tarsi 120, 122 are composed of dense irregular connective tissue and are responsible for the architectural form of the lids. The superior tarsus 122 extends across the length of the eyelid from the lateral edge to the medial side of the eye. The superior tarsus 122 may be about, for example, 10 mm wide in the central lid and narrows medially and laterally. The inferior tarsus 120 is substantially the same length as the superior tarsus, but narrower at the center of the lid. It also narrows medially and laterally from the center of the lid. The conjunctiva 140 is very adherent to the underlying tarsus. In addition to joining with the skin at the lid margin, the conjunctiva 140 lies adjacent to the superior and inferior tarsi 120, 122.

The eyelid crease 112 is typically located at or near the superior border of the tarsus 122. The skin below the crease 112 is firmly attached to the underlying tarsus 122 via attachments of the elevator aponeurosis 128. The aponeurosis 128 has anterior projections through orbicularis oculi muscle 116 to the skin 108 and connections to tarsus 122. Above the crease 112, the skin is more mobile because of its lack of superior aponeurotic attachments and relatively loose attachment to the underlying orbital septum 142. The lower eyelid 42 also has a crease 114. It generally marks the inferior border of the tarsus 120.

The orbicularis oculi muscle 116, 118 of the upper and lower eyelid 40, 42 is divided arbitrarily into orbital and palpebral portions; the palpebral portion is further divided into preseptal and pretarsal portions. The pretarsel portions are shown at reference numbers 124, 126, respectively, for the upper and lower eyelids. The orbital portions extend beyond the orbital rim to overlie the frontalis, temporalis, and cheek musculature. The pretarsal orbicularis oculi muscles are located anterior to the tarsi 122, 120 to which they are firmly attached. The superior pretarsal muscle is securely bound between the levator aponeurosis 128 and overlying skin 108 by anterior fibrous projections of the levator 128. These projections are found from the crease 112 down to the lid margin. The superior and inferior pretarsal muscles 124, 126 give rise laterally to the lateral canthal tendon and insert on the medial orbit wall via the medial canthal tendon.

The orbital septum is a mesodermal layer of the embryonic lid. In the upper lid, the septum 142 attaches to the levator aponeurosis 128 above the superior border of the tarsus 122. In the lower lid, the septum 144 attaches to the inferior edge of the tarsus 120.

The retractors of the eyelids collectively serve to open the eyelids. The levator muscles include the levator aponeurosis 128 and a posterior superior tarsal muscle layer (Müller's muscle) 130. The aponeurosis 128 spreads medially and laterally to form the horns of the levator. The lower end of the aponeurosis 128 inserts into the lower third of the anterior surface of the tarsus 122. The Müller's muscle attaches to the superior margin of the tarsus 122.

Lower eyelid retractors include the capsulopalpebral facia 146. This facia 146 extends anteriorly to fuse with the orbital septum and inserts on the lower border of the tarsus 120 as well as the anterior and posterior surfaces. Some anterior projections of the facia may penetrate the orbicularis muscle and contribute to the formation and maintenance of the lower eyelid transverse crease 114. Just posterior to the facia 146 is the sympathetically innervated inferior tarsal muscle (Müller's muscle) 132. The Müller's muscle 132 is believed to terminate beneath the inferior border of tarsus 120.

Stimulation of a denervated facial muscle to restore function, even eyelid function, is currently known. For example, the article "Control of Paralyzed Axial Muscles by Electrical Stimulation" by Zealear, D. L. and H. H. Dedo, *Acta Otolaryngol* 83: pages 514–527, 1977, describes a closed loop system where muscle activity from the intact side of the face is used to initiate stimulation on the denervated side. French patent No. 74 26103 (Publication No. 2 279 376) entitled "Process of Controlling Muscular Contraction on the Paralyzed Side of the Face Struck with Unilateral Paralysis and Apparatus/Devices Used to Realize This Process," to Elbaz and Delerm, published 20 Feb. 1976, describes a device which monitors the muscle activity of the intact side to control the stimulus timing of the injured, denervated side. Additionally, U.S. Pat. No. 4,799,487, issued 24 Jan. 1989 to Bleicher, and entitled "Reanimation Device and Method for Treating a Paralyzed Face" describes a microprocessor system which performs substantially the same functions described in the article by Zealear, et al., and the French Patent No. 74 26103. Further, for example, an article entitled "Electronic Reanimation of Facial Paralysis—A Feasibility Study," by Rothstein and Berlinger, *Otolarynaoloy-Head and Neck Surgery*, Vol. 94, No. 1 (January 1986) describes a similar concept where he demonstrated the ability to mirror blink activity.

However, for any such stimulus system to be efficiently utilized, the electrode for the system must be designed such that it can be easily implanted, is chronically stable once implanted, and provides electrical stimulation without causing pain to the patients. For example, it is important to avoid stimulation of surrounding facial muscles or nearby sensory nerves, such as, for example, the supraorbital nerve located above the eyelid; the supratrochlear artery, medial to the supraorbital nerve above the eyelid; and the infraorbital nerve located below the lower eyelid. Current known electrodes do not provide all of such functionality as applicable to the eyelid, eye, and surrounding area.

For the reasons indicated above and for other reasons which become apparent from the detail below, improved implantable eyelid electrode devices and methods of implanting such devices are needed. It is therefore, the object of the present invention to provide such electrodes and methods for implanting such electrode devices.

SUMMARY OF THE INVENTION

An electrode apparatus for implanting in an eyelid is described. The electrode apparatus includes a body of nonconductive material having first and second edges and first and second ends. A longitudinal axis extends between the first and second ends and a distance from the longitudinal axis to at least one of the first and second edges decreases towards at least one of the first and second ends. The electrode apparatus also includes conductive material positioned at a surface of the body of nonconductive material and at least one lead wire in electrical contact with the conductive material.

In one embodiment, the distance from the longitudinal axis to at least one of the first and second edges decreases towards each of the first and second ends in order to conform to the shape of the eyelid. In further embodiments, the first and second edges may be either convex or concave shaped.

In another embodiment of the electrode apparatus, the apparatus includes a body of nonconductive material having first and second edges and first and second ends. A longitudinal axis extends between the first and second ends. The electrode apparatus further includes a plurality of strip conductive electrodes with each conductive electrode having a predetermined length. A conductive electrode is positioned along the longitudinal axis with its length perpendicular to the longitudinal axis. A lead wire is in electrical contact with each conductive electrode. In a further embodiment of this apparatus, each of the plurality of conductive electrodes is capable of being connected as an anode, a cathode, or left in an open configuration.

In another embodiment of this apparatus, the plurality of conductive electrodes includes at least three conductive electrodes. One of the at least three electrodes is connected as an active electrode centrally located between two current guarding electrodes.

In a further embodiment of this apparatus, the conductive electrodes are recessed in the surface of the nonconductive body. Preferably, the conductive electrodes are recessed below the surface of the nonconductive body.

In another implantable electrode apparatus of the invention, the apparatus includes a first electrode array and a second electrode array. Both the first and second electrode arrays include nonconductive bodies having a longitudinal axis between a first and second end, and also have first and second edges. A plurality of strip conductive electrodes are positioned along the longitudinal axis and having a length perpendicular thereto. Further, each of the first and second electrode arrays include lead wires in electrical contact with each conductive electrode. The second electrode is narrower than the first electrode.

A method for implanting an electrode apparatus is also disclosed. The method includes providing an implantable eyelid electrode having a body of nonconductive material conformably shaped to the shape of an eyelid. Conductive material is positioned at the surface of the body of nonconductive material and at least one lead wire is in electrical contact with the conductive material. The implantable eyelid electrode is positioned adjacent the orbicularis oculi muscle fibers such that the conductive material of the implantable eyelid electrode is adjacent to the muscle fibers. In one embodiment of the method, the implantable eyelid electrode is positioned behind or posterior to the pretarsal orbicularis muscle fibers.

DETAILED DESCRIPTION OF THE PREFERRED EMBODIMENTS

Figure 1:
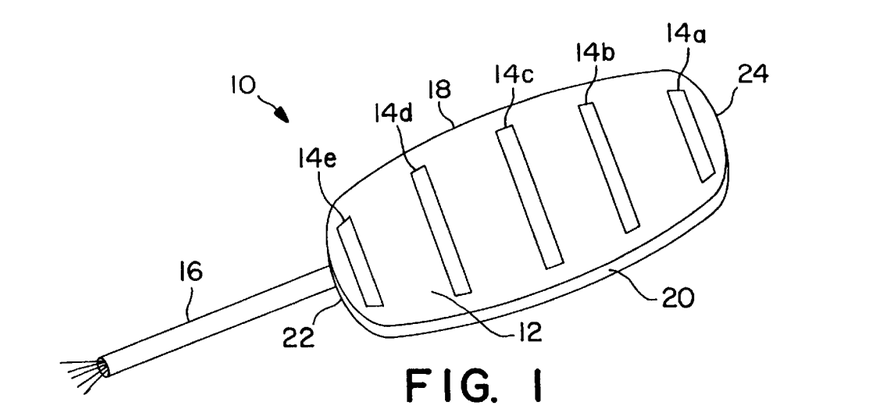
FIG. 1 is a perspective view of an implantable eyelid electrode in accordance with the present invention.
Figure 2:
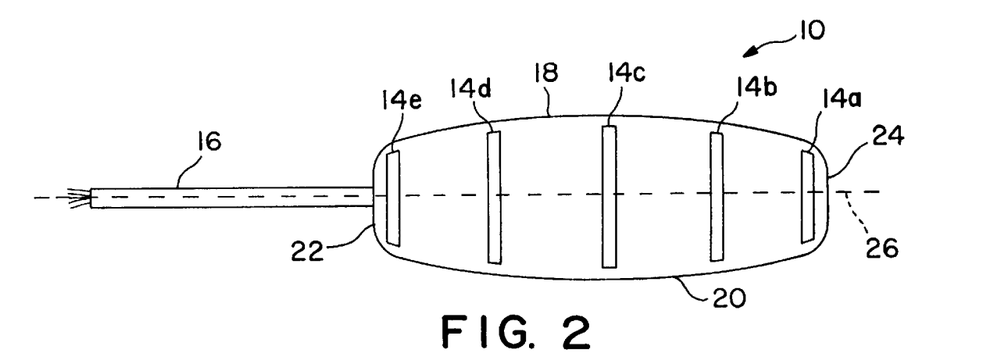
FIG. 2 is a top plan view of the electrode of FIG. 1.
Figure 3:
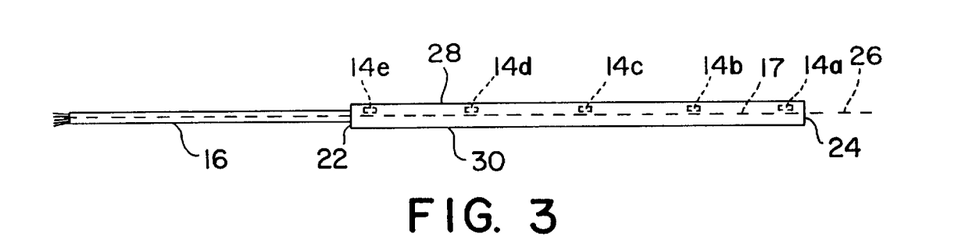
FIG. 3 is a front view of the electrode of FIG. 1.

Referring to the FIGS. 1–3, an implantable eyelid electrode array 10 in accordance with the present invention shall be described. The implantable eyelid electrode array 10 includes an insulating backing or a body of nonconductive material 12 having a shape and mechanical properties easily and comfortably accommodated by the eyelid. For example, the body of nonconductive material 12 has a reduced size at the ends thereof to accommodate the shape of the eyelid at the medial and temporal portions of the eye. The implantable eyelid electrode array 10 further includes conductive material or conductive electrodes 14 positioned at the surface of the body of nonconductive material 12. A separate lead wire 16 is in electrical contact with each conductive electrode 14 such that each conductive electrode 14 can be connected to a stimulator 200 (FIG. 4) by way of a switching apparatus 210 (FIG. 4) as an anode, a cathode, or in an unused or open configuration.

The implantable eyelid electrode array 10 is configured to activate the paralyzed denervated orbicularis oculi muscle of patients suffering from hemifacial paralysis. Since the electrode array 10 is designed to activate a thin layer of paralyzed muscle, the width of the array and the length of the individual conductive electrodes or tabs 14 are preferably as large as possible in order to contact as many fibers as possible, yet shaped to adapt and form comfortably to the eyelid. However, such stimulation of the eyelid muscle fibers must be performed with the objective of limiting current from stimulating adjacent sensory nerves and motor nerves innervating the levator muscles while stimulating or treating the hemifacial paralysis. The various stimulated thresholds for denervated muscle fibers are significantly higher than the nerve fibers; therefore, the need for limiting the current spread to prevent any adverse sensation is important. Further, such an electrode may be utilized for conditioning of the eye or eyelid instead of a blink stimulation. For example, the electrode array 10 may be used for conditioning by post-tetanic potentiation, which includes stimulation of nerves to make them more effective, as is known to one skilled in the art.

The implantable eyelid electrode array 10 which includes the body of nonconductive material 12, the conductive material or electrodes 14, and the leads in electrical contact with the conductive electrodes 14, provides an implantable device that maintains a more uniform current density over the electrode surface. Further, it prevents current spread to surrounding facial muscles or nearby sensory nerves, thus avoiding undesirable stimulation of these areas. The body of nonconductive material 12 includes a longitudinal axis 26 extending between a first end 22 and a second end 24. Further, the body of nonconductive material 12 includes a first edge 18 and a second edge 20.

The insulated backing or thin flat body of nonconductive material 12 may be of any suitable biocompatible material; for example, the material may be silicone rubber or polyurethane. The thickness of the flat body of nonconductive material 12 is less than 1.5 mm and preferably less than 1 mm. Other thicknesses of the body may be suitable; however, they must not degrade the surrounding tissue upon and after implantation. The nonconductive material is stiff enough to allow insertion through a stab wound, but flexible enough to allow conformance to the eye structure after implantation.

In addition, the body of nonconductive material 12 can be a perforated material to aid tissue in growth and adhesion. Suture holes can be provided in the thin flat body of nonconductive material 12 for attaching and holding the electrode array 10 in a position in the eyelid. Further, other materials that provide beneficial tissue adherence can be utilized. For example, Dacron tabs could be utilized to aid adhesion. Such tabs could be embedded in the body of nonconductive material 12 and allowed to extend from the edges thereof.

The shape of the body of the nonconductive material 12 is of a shape suitable for adaptation of the electrode array 10 to the eyelid and is of such width and length to accommodate conductive electrodes 14 such that as many fibers as possible can be contacted with the electrode array 10. The body of nonconductive material 12 may take one of any number of shapes or configurations. As shown in FIG. 2, the first and second ends include a length which lies perpendicular to the longitudinal axis 26. The first edge 18 and the second edge 20 take a convex shape relative to the longitudinal axis 26. The distance between the longitudinal axis and the first edge 18 decreases towards both the first end 22 and the second end 24. The same is true with respect to the distance between the longitudinal axis 26 and the second edge 20.

Figure 5:
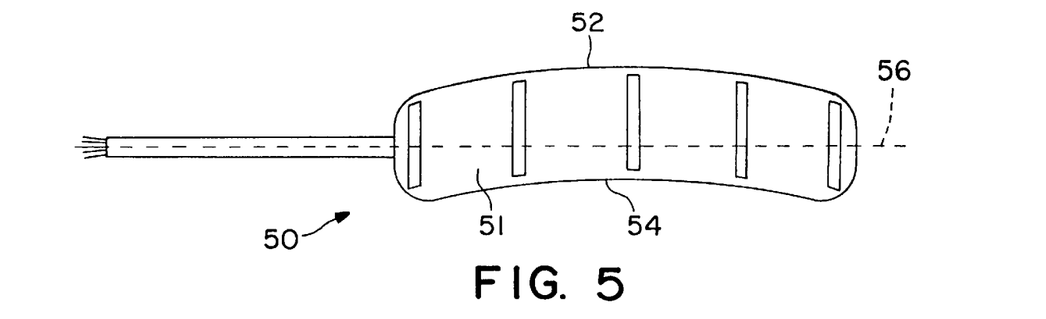
FIG. 5 is a top plan view of an electrode showing an alternative shape of the implantable eyelid electrode of the present invention.
Figure 6:
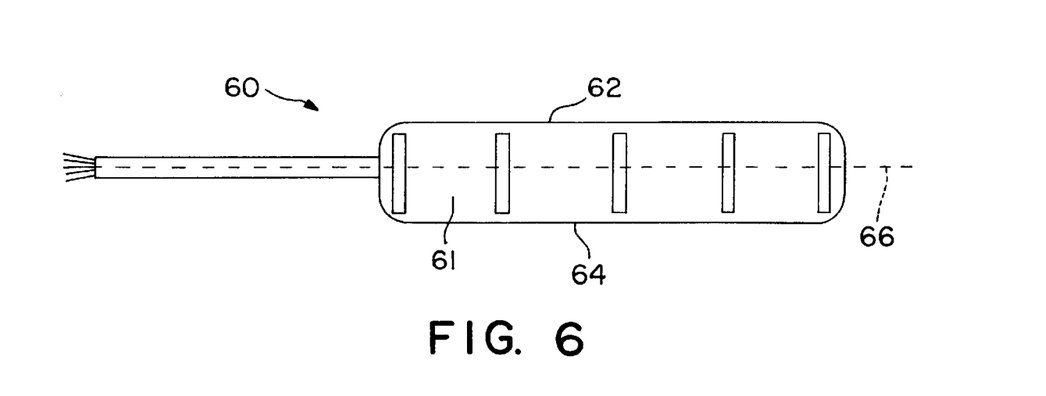
FIG. 6 is a top plan view of an alternative shape of an implantable eyelid electrode in accordance with the present invention.

Alternative configurations for the shape of the body of nonconductive material 12 are shown in FIGS. 5 and 6. In FIG. 5, the implantable eyelid electrode array 10 includes a body of nonconductive material 51 wherein a first edge 52 takes a convex shape relative to longitudinal axis 56. Second edge 54 takes a concave shape relative to longitudinal axis 56. The implantable eyelid electrode array 60, as shown in FIG. 6, includes a body of nonconductive material 61 in which the first edge 62 and second edge 64 are substantially parallel to the longitudinal axis 66.

Although, in the preferred embodiment shown in FIGS. 1–3, the distance between the first edge 18 and second edge 20 is decreased towards both the first end 22 and second end 24, many other configurations are suitable for use. For example, as shown in the alternative embodiments of FIGS. 5 and 6, the edges of the body of nonconductive material may take concave, convex, or parallel shapes and also the body may be narrowed to either one end or the other. Further, the body of nonconductive material may be more elliptical in shape or even circular. The present invention is not limited to only those shapes shown in the figures herein, but is limited only as described in the accompanying claims.

As shown in FIG. 3, the implantable eyelid electrode array 10 includes an upper surface 28 and a lower surface 30. Five conductive electrodes 14 are positioned at the upper surface 28 of the nonconductive body 12. The conductive electrodes 14 may be of any suitable conductive material for use in implantable electrode devices, such as, for example, stainless steel, conductive polymers, and platinum iridium foil. Preferably, the material is platinum iridium foil. As an alternative to individual conductive electrodes 14, a wire mesh of, for example, platinum iridium foil, may be utilized on the upper surface 28 of the body of nonconductive material 12 to provide the function of the conductive material.

The conductive electrodes 14 are thin and narrow electrodes. The length of each of the electrodes is a direct function of the distance between the first edge 18 and second edge 20 of the body of nonconductive material 12. Therefore, as shown in FIG. 2, the conductive electrode 14c at the center of the body of nonconductive material 12 is longer than the other electrodes positioned towards the first and second ends 22, 24. The other electrodes decrease in length as the distance between the first edge 18 and second edge 20 is narrowed towards the first end 22 and second end 24. The conductive electrodes 14 are positioned along the longitudinal axis 26 with their length lying perpendicular to the longitudinal axis 26. The conductive electrodes 14 are positioned perpendicular to the longitudinal axis 26 to facilitate the passing of current parallel to the muscle fibers, i.e. orbicularis oculi muscle fibers, in the eyelid which run from the medial to the temporal portion of the eye. By having the current pass parallel to the muscle fibers, low thresholds of stimulation are achieved.

The conductive electrodes 14 are each positioned at the upper surface 28 of the body of nonconductive material 12 to achieve a uniform electrode current distribution and to decrease the possibility of tissue damage with the high stimulus levels necessary to stimulate denervated muscle. To achieve such functions, the electrodes are recessed slightly below the upper surface 28. Although such positioning of conductive electrodes 14 is preferable, other alternative positions may also be suitable. For example, the conductive electrodes 14 may be positioned on the upper surface 28 or level with the upper surface 28.

Although the shape of the conductive electrodes 14 are preferably thin and narrow electrodes of rectangular-like shape, other shapes of electrodes may also be suitable. For example, circular electrodes, elliptical shaped electrodes, or any other geometric shape which may provide suitable stimulation.

In addition, although the electrode array 10 includes five conductive electrodes 14, any number of conductive electrodes may be utilized. For example, the number of electrodes may be 8, 4, or even 1 electrode. Although the number of electrodes 14 may vary, each of the electrodes is in electrical contact with at least one wire lead. For example, wire lead 17 is connected to the electrode 14a closest to second end 24, and each of the other conductive electrodes 14b–e would be electrically connected to other separate lead wires. The other separate lead wires are then brought out from the body of nonconductive material 12 as lead 16. Thin wire leads, such as lead 17, may include any appropriate lead wires such as stainless steel, or MP-35N wire with PTFE insulation used where necessary as bundled in lead 16. The wire leads of the lead 16 are then connected to the switching apparatus 210 (FIG. 4) which is connected to a stimulator 200 (FIG. 4) or impulse generating device. The implantable eyelid electrode array 10, in accordance with the present invention, may be utilized with any stimulator, such as an implantable pulse generator (IPG) (for example, implanted in the mastoid), a standard pacing unit, or a stimulator controlled from the intact side of the face. The present invention is not limited to any particular stimulator and is only limited in accordance with the invention as described in accompanying claims.

The switching apparatus 210 (FIG. 4) allows the conductor electrodes 14a–e to be connected as either anodes, cathodes, or in an open configuration, i.e., unused. In the preferred embodiment, in order to minimize current spread, a guarded multipolar configuration of the conductive electrodes 14 is utilized. For example, conductive electrodes 14a and 14e could be positive, while electrode 14c could be negative. In another configuration, electrode 14c could be connected as the active electrode with conductive electrodes 14b and 14e being the two current guarding electrodes. Other guarded multipolar configurations may be used and the particular guarded multipolar configuration utilized will be dependent upon which configuration prevents current spread more effectively such as to the supraorbital, infraorbital, and supratrochlear nerves located about the eye.

Figure 4:
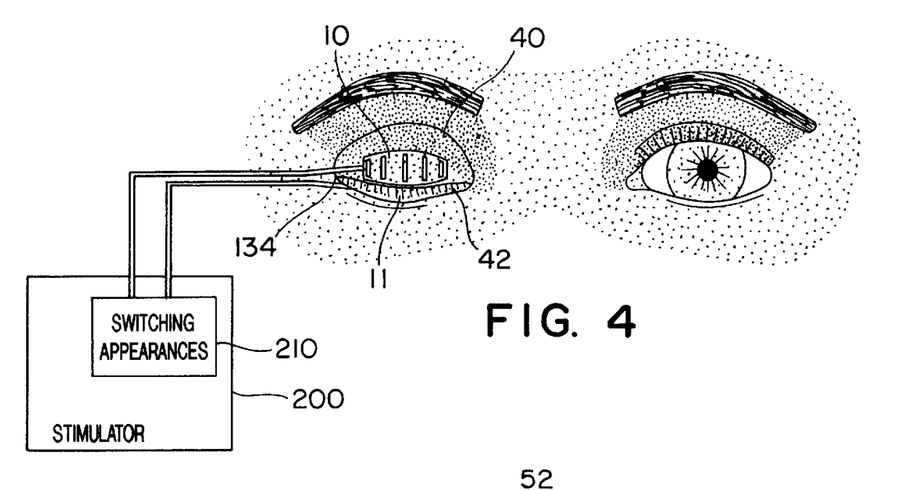
FIG. 4 is a cutaway illustration of the position of an electrode of FIG. 1 at the upper eyelid and also an electrode positioned at the lower eyelid.

As shown in FIG. 4, two implantable eyelid electrode arrays 10, 11 are be utilized in accordance with the present invention. Implantable eyelid electrode array 10 is implanted in upper eyelid 40 of a patient, and a narrower implantable eyelid electrode array 11 is implanted in lower eyelid 42. In accordance with the present invention, because of the different shape and size of the upper and lower eyelid, the electrode arrays implanted therein are also of different shape and size. For example, the width between the first and second edges of the electrode array 11 implanted in the lower eyelid 42 is narrower than the width of the electrode array 10 implanted in the upper eyelid 40. Further, the shape of the eyelid electrode array 11 may be different. For example, the first edge of the eyelid electrode array 11 may be concave in shape to adapt comfortably to the lower eyelid.

It should be apparent to one skilled in the art that both the eyelid electrode array 10 and eyelid electrode array 11 may take any shape and configuration as described above. For example, the electrode arrays may have a different number of conductive electrodes, the electrodes may be of different shape and configuration, the connection of the conductive electrodes to the stimulator may be different, the shape of the body of nonconductive material may be different, etc.

FIG. 4, a cutaway view of the upper and lower eyelid 40, 42, show the position on the eyelids where the implantable eyelid electrode arrays 10 and 11 are implanted. FIG. 7 is a cross-sectional view of the eye showing the implantable electrode arrays 10 and 11 as implanted behind the tarsal orbicularis oculi muscles 124 and 126, respectively.

In the method of implanting the implantable eyelid electrode array 10, a stab wound or incision is made in the crease 112 on the upper eyelid 42. The implantable eyelid array 10 is stiff enough to allow insertion through the incision. The eyelid electrode array 10 is then positioned behind the tarsal orbicularis oculi muscle 124 adjacent the tarsus 122. The conductive electrodes 14 of the implantable eyelid electrode array 10 lie adjacent to the posterior surface of the tarsal orbicularis oculi muscle fibers 124. The location of the eyelid electrode behind or posterior to the superior tarsal orbicularis oculi muscle fibers 124 is preferred in order to avoid stimulation of surrounding facial muscles or nearby sensory nerves. Further, this position gives direct stimulation to the muscles of the eyelid which most effectively close the eye, including stimulation for movement of the levator aponeurosis and Müller's muscle 130.

The electrode array 10, in its configuration as shown in FIG. 1, is orientated so that the conductive electrodes 14 have their lengths perpendicular to the orbicularis oculi muscle fibers 124. The current then passes parallel to these muscle fibers in order to obtain the lowest necessary stimulation thresholds. In order to minimize current spread, the guarded multipolar configuration is used, as previously described. Further, the insulating backing, or body of nonconductive material, prevents current spread to undesired portions of the eyelid. After the electrode array is positioned between the tarsus 122 and tarsal orbicularis oculi muscle fibers 124, the lead is brought out to exit the eyelid 40 by way of the lateral or temporal canthus 134 through a puncture wound, as best shown in FIG. 4.

The position of the eyelid electrode array 11 is also shown in FIG. 7 behind the inferior tarsal orbicularis oculi muscle 126. The method of implanting the electrode array 11 is very similar to the implant of the electrode array 10, with an incision or stab wound being made in crease 114 of the lower eyelid 42 and insertion of the electrode array 11 through the incision and into a position behind the inferior tarsal orbicularis oculi muscle 126. The conductive electrodes are adjacent to the posterior surface of the inferior tarsal orbicularis oculi muscle fibers with the body of nonconductive material preventing current spread to undesired portions of the eyelids and surrounding area and focusing the current in the muscle fibers 126. As with the electrode array 11, the lead of the electrode array 11 is brought out the lateral canthus 134 of the eye.

It should be apparent to one skilled in the art, that in addition to implanting behind the tarsal orbicularis oculi muscle 124 of the upper eyelid 40, the implantable eyelid electrode arrays 10 may be implanted between the skin 108 and superior orbicularis oculi muscle fibers 124, with the conductive electrodes being adjacent to the anterior surface of muscle fibers 124. In this manner, the body of nonconductive material would prevent current spread to the overlying skin and focus the current into the underlying muscle fibers 124. Further, the electrode array 11 may also be implanted between the skin 110 and inferior tarsal orbicularis oculi muscle 126 with the conductive electrodes adjacent to the anterior surface of the muscle fibers 126. Again, in this matter, the body of nonconductive material prevents current spread to the overlying skin 110 and focuses the current into the muscle fibers 126.

Further, it should be recognized by one skilled in the art that there may be other locations on the eye which would benefit from the implanting of such an electrode without stimulation of undesirable portions about the eye. For example, the electrode array may be implanted adjacent any portion of the orbicularis oculi muscle for simulation thereof.

It will be appreciated by those skilled in the art that while the invention has been described above in connection with particular embodiments and examples, the invention is not necessarily so limited in that numerous other embodiments, examples, uses, modifications, and departures from such embodiments, examples and uses may be made without departing from the inventive concepts as described herein in the accompanying claims.

We claim:

1. An electrode apparatus for implanting in an eyelid, the apparatus comprising:

a) a body of nonconductive material having first and second edges and first and second ends, in which (1) a longitudinal axis extends between the first and second ends, and
(2) a distance from the longitudinal axis to at least one of the first and second edges decreases towards at least one of the first and second ends to conform to the shape of an eyelid;
b) conductive material positioned at a surface of the body of nonconductive material; and
c) at least one lead wire in electrical contact with the conductive material.

2. An electrode apparatus for implanting in an eyelid, the apparatus comprising:
a) a body of nonconductive material having first and second edges and first and second ends, conformably adapting to the curvature of the eyelid when implanted, in which
(1) a longitudinal axis extends between the first and second ends, and
(2) a distance from the longitudinal axis to at least one of the first and second edges decreases towards at least one of the first and second ends;
b) conductive material positioned at a surface of the body of nonconductive material; and
c) at least one lead wire in electrical contact with the conductive material.

3. An electrode apparatus for implanting in an eyelid, the apparatus comprising:
a) a body of nonconductive material having first and second edges and first and second ends, in which
(1) a longitudinal axis extends between the first and second ends,
(2) a distance from the longitudinal axis to at least one of the first and second edges decreases towards at least one of the first and second ends;
b) conductive material positioned at a surface of the body of nonconductive material and including at least one strip electrode positioned along the longitudinal axis to have a length lying substantially perpendicular to muscle fibers extending from the lateral part of the eyelid to the medial part of the eyelid; and
c) at least one lead wire in electrical contact with the conductive material.

4. An electrode apparatus for implanting in an eyelid, the apparatus comprising:
a) a body of flexible nonconductive material having first and second edges and first and second ends, substantially thin enough to lie within the eyelid when implanted, and comprising
(1) a longitudinal axis extending between the first and second ends;
(2) a plurality of strip conductive electrodes, each conductive electrode having a predetermined length, at least one of the conductive electrodes being positioned along and perpendicular to the longitudinal axis; and
b) a lead wire in electrical contact with each conductive electrode.

5. The apparatus according to claim 1 or 2 or 3 or 4, in which the one of the first and second edges is convex in shape.

6. The apparatus according to claim 5, in which the other of the first and second edges is concave in shape.

7. The apparatus according to claim 5, in which both of the first and second edges are convex in shape.

8. The apparatus according to claim 1 or 2 or 3 or 4, in which one of the first and second edges is concave in shape.

9. The apparatus according to claim 1 or 3 or 4, in which the nonconductive body is a flexible material for conformably adapting to the curvature of the eyelid when implanted.

10. The apparatus according to claim 1 or 2 or 3 or 4, in which the nonconductive body includes an adhesion promoting material.

11. The apparatus according to claim 8, in which the adhesion promoting material is a perforated material.

12. The apparatus according to claim 1 or 2 or 3 or 4, in which the nonconductive body includes suture holes.

13. The apparatus according to claim 1 or 2 or 3 or 4, in which the conductive material includes a plurality of conductive electrodes, any one of the electrodes capable of being connected as an anode, a cathode, or left in an open configuration.

14. The apparatus according to claim 13, in which each conductive electrode is a strip electrode and each conductive electrode is positioned with its length perpendicular to and at a location along the longitudinal axis.

15. The apparatus according to claim 13, in which the plurality of conductive electrodes include at least three conductive electrodes, in which one of the at least three electrodes is an active electrode centrally located between two current guarding electrodes.

16. The apparatus according to claim 13, in which each of the plurality of conductive electrodes has a length, the length of each conductive electrode being a function of the distance between the first and second edges, the conductive electrodes being shorter as the distance between the first and second edges decreases.

17. The apparatus according to claim 16, in which the conductive electrodes are recessed in the surface of the nonconductive body.

18. The apparatus according to claim 17, in which the conductive electrodes are recessed below the surface of the nonconductive body.

19. The apparatus according to claim 1 or 2 or 4, in which the conductive material includes at least one strip electrode positioned along the longitudinal axis to have a length lying substantially perpendicular to muscle fibers extending from the lateral part of the eyelid to the medial part of the eyelid.

20. The apparatus according to claim 1 or 2 or 3 or 4, in which the conductive material is recessed in the surface of the nonconductive material.

21. The apparatus according to claim 20, in which the conductive material is recessed below the surface of the nonconductive material.

22. An eyelid stimulation system, comprising
a) a pulse generator; and
b) the apparatus according to claim 1 or 2 or 3 or 4, in which the body of nonconductive material, the conductive material positioned at the surface of the body of nonconductive material, and at least one lead wire in electrical contact with the conductive material form a first electrode adapted for implanting in an upper eyelid and connection to the pulse generator; and in which the electrode apparatus further includes a second electrode having a body of nonconductive material, conductive material positioned at a surface of the body of nonconductive material, and at least one lead wire in electrical contact with the conductive material, the second electrode adapted for implanting in a lower eyelid and also for connection to the pulse generator, the distance between the first and second edges of the first electrode along the longitudinal axis being greater than the distance between first and second edges of the second electrode; in which the first and second electrodes and the pulse generator are electrically connected such that the pulse generator may stimulate at least one of the upper and lower eyelids through at least one of the respective first and second electrodes.

23. An electrode apparatus for implanting in an eyelid, the apparatus comprising:
   a) a body of nonconductive material having first and second edges and first and second ends defining a longitudinal axis extending between the first and second ends, a distance from the longitudinal axis to at least one of the first and second edges decreasing toward at least one of the first and second ends to conform to the shape of the eyelid;
   b) a plurality of strip conductive electrodes, each conductive electrode of a predetermined length, at least one of the conductive electrodes positioned along and perpendicular to the longitudinal axis; and
   c) a lead wire in electrical contact with each conductive electrode.

24. An electrode apparatus for implanting in an eyelid, the apparatus comprising:
   a) a body of flexible nonconductive material conforming to the shape of an eyelid, having first and second edges and first and second ends defining a longitudinal axis extending between the first and second ends;
   b) a plurality of strip conductive electrodes, each conductive electrode having a predetermined length, at least one of the conductive electrodes being positioned along and perpendicular to the longitudinal axis; and
   c) a lead wire in electrical contact with each conductive electrode.

25. An electrode apparatus for implanting in an eyelid, the apparatus comprising:
   a) a body of flexible nonconductive material having first and second edges and first and second ends defining a longitudinal axis extending between the first and second ends;
   b) a plurality of strip conductive electrodes, each conductive electrode having a predetermined length, at least one of the conductive electrodes dimensioned and positioned along, and perpendicular to, the longitudinal axis to lie substantially perpendicular to muscle fibers extending from the lateral part of the the eyelid to the medial part of the eyelid; and
   c) a lead wire in electrical contact with each conductive electrode.

26. An electrode apparatus for implanting in an eyelid, the apparatus comprising:
   a) a body of flexible nonconductive material having first and second edges and first and second ends, substantially thin enough to lie within the eyelid when implanted, and comprising a longitudinal axis extending between the first and second ends;
   b) a plurality of strip conductive electrodes, each conductive electrode having a predetermined length, at least one of the conductive electrodes being positioned along and perpendicular to the longitudinal axis; and
   c) a lead wire in electrical contact with each conductive electrode.

27. The apparatus according to claim 23 or 24 or 25 or 26, in which each of the plurality of conductive electrodes is capable of being connected as an anode, a cathode, or left in an open configuration.

28. The apparatus according to claim 27, in which the plurality of conductive electrodes include at least three conductive electrodes, one of the at least three electrodes is an active electrode centrally located between two current guarding electrodes.

29. The apparatus according to claim 23 or 24 or 25 or 26, in which the conductive electrodes are recessed in a surface of the nonconductive body.

30. The apparatus according to claim 29, in which the conductive electrodes are recessed below the surface of the nonconductive body.

31. The apparatus according to claim 23 or 24 or 25, or 26, in which the distance from the longitudinal axis and one of the first and second edges decreases towards at least one of the first and second ends.

32. The apparatus according to claim 31, in which the length of each conductive electrode is a function of the distance between the first and second edges with the conductive electrodes becoming shorter as the distance between the first and second edges decreases towards at least one of the first and second ends.

33. An implantable eyelid stimulation system comprising:
   a) a pulse generator; and
   b) by a first implantable electrode array adapted for electrical connection to the pulse generator, including a nonconductive body having a longitudinal axis between a first and second end and having first and second edges, a plurality of strip conductive electrodes positioned along and perpendicular to the longitudinal axis, and a lead wire in electrical contact with each conductive electrode; and
   c) a second implantable electrode array adapted for electrical connection to the pulse generator, including a nonconductive body having a longitudinal axis extending between a first and second end and having first and second edges, a plurality of strip conductive electrodes positioned along and perpendicular to the longitudinal axis, and a lead wire in electrical contact with each conductive electrode, the nonconductive body of the second electrode array being of a narrower configuration than nonconductive body of the first electrode array;
   in which the first and second electrodes and the pulse generator are electrically connected such that the pulse generator may stimulate at least one of the upper and lower eyelids through at least one of the respective first and second electrodes.

34. The apparatus according to claim 33, in which in at least one of the first and second electrode arrays, the distance between the longitudinal axis and one of the first and second edges decreases towards at least one of the first and second ends.

35. The apparatus according to claim 34, in which each conductive electrode has a length, the length being a function of the distance between the first and second edges of the nonconductive body with the length of the conductive electrodes being shorter as the distance between the first and second edges decreases.

36. A method for implanting an electrode apparatus, the method comprising the steps of:
   a) providing an implantable eyelid electrode having a body of nonconductive material conformably shaped to the shape of an eyelid, conductive material positioned at a surface of the body of nonconductive material, and at least one lead wire in electrical contact with the conductive material;
   b) implanting the electrode adjacent the orbicularis oculi muscle fibers such that the conductive material of the implantable eyelid electrode is adjacent the muscle fibers.

37. The method according to claim 36, in which the implanting step includes the steps of:

a) making an incision in a crease of the eyelid;

b) inserting the implantable eyelid electrode through the incision and placing the electrode adjacent the orbicularis oculi muscle fibers such that the conductive material of the implantable eyelid electrode is adjacent the muscle fibers; and c) bringing the at least one lead wire out the lateral canthus.

38. The method according to claim 36, in which the step of inserting the implantable eyelid electrode comprises positioning the electrode behind the pretarsal orbicularis muscle fibers.

39. The method according to claim 38, further including an additional implantable eyelid electrode including a body of nonconductive material conformably shaped to the shape of a lower eyelid, conductive material positioned at a surface of the body of nonconductive material, and at least one lead wire in electrical contact with the conductive material, the nonconductive body of the additional implantable eyelid electrode having a shape that is narrower than the implantable eyelid electrode implanted in an upper eyelid; and further in which the method includes positioning the additional electrode behind the pretarsal orbicularis oculi muscle fibers of the lower eyelid with the surface of the nonconductive body at which the conductive material is positioned being adjacent to the pretarsal orbicularis muscle.

40. The method according to claim 36, in which the conductive material includes a plurality of conductive electrodes, a separate lead wire being in contact with each conductive electrode of the plurality of electrodes; and further in which the method includes connecting the conductive electrodes via the lead wires as either an anode or cathode, or leaving the conductive electrode in an open configuration.

41. The method according to claim 36, in which the step of providing an implantable eyelid electrode comprises providing an electrode in which the nonconductive body is a flexible material for conformably adapting to the curvature of the eyelid.

42. The method according to claim 36, in which the step of providing an implantable eyelid electrode comprises providing an electrode in which the body of nonconductive material includes first and second edges and first and second ends with a longitudinal axis extending between the first and second ends; further in which the step of providing an implantable eyelid electrode comprises providing an electrode in which the conductive material includes a plurality of strip conductive electrodes, each conductive electrode of a predetermined length, the conductive electrodes positioned along the longitudinal axis with its length perpendicular to the longitudinal axis.

43. The method according to claim 42, in which the step of providing an implantable eyelid electrode comprises providing an electrode in which the conductive material is recessed below the surface of the nonconductive material.

44. The method according to claim 42, in which the step of providing an implantable eyelid electrode comprises providing an electrode in which the plurality of conductive electrodes include at least three conductive electrodes, one of the at least three electrodes is an active electrode centrally located between two current guarding electrodes.

45. The method according to claim 42, in which the step of providing an implantable eyelid electrode comprises providing an electrode in which the distance from the longitudinal axis and one of the first and second edges decreases towards at least one of the first and second ends.

46. The method according to claim 45, in which the step of providing an implantable eyelid electrode comprises providing an electrode in which the length of each conductive electrode is a function of the distance between the first and second edges with the conductive electrodes becoming shorter as the distance between the first and second edges decrease towards at least one of the first and second ends.

47. An apparatus for blink stimulation of an eyelid, the apparatus comprising:

a) a body of nonconductive material having first and second edges and first and second ends, in which a longitudinal axis extends between the first and second ends and a distance from the longitudinal axis to at least one of the first and second edges decreases towards at least one of the first and second ends to conform to the shape of an eyelid;

b) conductive material positioned at a surface of the body of nonconductive material;

c) at least one lead wire in electrical contact with the conductive material; and d) a pulse generator electrically connected to the at least one lead wire.

48. The apparatus according to claim 47, in which the conductive material includes a plurality of strip conductive electrodes being positioned at locations along the longitudinal axis such that when implanted at least one of the electrodes has a length lying substantially perpendicular to muscle fibers extending from the lateral part of the eyelid to the medial part of the eyelid.

49. The apparatus according to claim 48, in which the pulse generator includes a switching apparatus for connecting the electrodes in various configurations.

50. The apparatus according to claim 49, in which the plurality of conductive electrodes includes at least three conductive electrodes, and further in which the switching apparatus connects one of the at least three electrodes as an active electrode centrally located between two current guarding electrodes.

\* \* \* \* \*

UNITED STATES PATENT AND TRADEMARK OFFICE
CERTIFICATE OF CORRECTION

PATENT NO. : 5,843,147
DATED : December 1, 1998
INVENTOR(S) : Roy L. Testerman, Donald J. Erickson, Ronald L. Mezera, Johann J. Neisz It is certified that error appears in the above-identified patent and that said Letters Patent is hereby corrected as shown below:

Column 12, Line 21, "by a first" should be "a first"

Signed and Sealed this

Sixth Day of June, 2000

*Attest:*

*Attesting Officer*

Q. TODD DICKINSON

*Director of Patents and Trademarks*